(12) United States Patent
Crouch

(10) Patent No.: US 11,413,343 B2
(45) Date of Patent: Aug. 16, 2022

(54) COCCIDIOSIS VACCINE

(71) Applicant: Intervet Inc., Madison, NJ (US)

(72) Inventor: Colin Crouch, High Wycombe (GB)

(73) Assignee: Intervet Inc., Madison, NJ (US)

( * ) Notice: Subject to any disclaimer, the term of this patent is extended or adjusted under 35 U.S.C. 154(b) by 0 days.

(21) Appl. No.: 16/913,857

(22) Filed: Jun. 26, 2020

(65) Prior Publication Data

US 2020/0323971 A1 Oct. 15, 2020

Related U.S. Application Data

(62) Division of application No. 16/064,027, filed as application No. PCT/EP2016/082530 on Dec. 23, 2016, now abandoned.

(30) Foreign Application Priority Data

Dec. 29, 2015 (EP) .................................... 15203012

(51) Int. Cl.
*A61K 39/012* (2006.01)
*A61K 39/00* (2006.01)

(52) U.S. Cl.
CPC ........ *A61K 39/012* (2013.01); *A61K 2039/54* (2013.01); *A61K 2039/542* (2013.01); *A61K 2039/552* (2013.01); *A61K 2039/55583* (2013.01)

(58) Field of Classification Search
CPC ............ A61K 39/012; A61K 2039/542; A61K 2039/55583; A61K 2039/54; A61K 2039/552
See application file for complete search history.

(56) References Cited

U.S. PATENT DOCUMENTS

| | | | |
|---|---|---|---|
| 5,055,292 A | 10/1991 | Mcdonald et al. | |
| 6,440,431 B1 | 8/2002 | Yoshida et al. | |
| 7,879,342 B2 | 2/2011 | McDougald et al. | |
| 2006/0165731 A1 | 7/2006 | McDonald et al. | |

FOREIGN PATENT DOCUMENTS

| | | | |
|---|---|---|---|
| CA | 2688613 A1 | 12/2008 | |
| CN | 1649602 A | 8/2005 | |
| CN | 1968658 A | 5/2007 | |
| CN | 101184500 A | 5/2008 | |
| CN | 102727900 A | 10/2012 | |
| EP | 0256878 A2 | 2/1988 | |
| EP | 2164496 A2 * | 3/2010 | ................ A61P 3/02 |
| EP | 2164496 B1 | 4/2017 | |
| JP | 2000239120 A | 9/2000 | |
| JP | 2006510671 A | 3/2006 | |
| WO | 2002037961 A2 | 5/2002 | |
| WO | 2003092706 A1 | 11/2003 | |
| WO | 2004052393 A1 | 6/2004 | |
| WO | 2005099617 A1 | 10/2005 | |
| WO | 2005123034 A2 | 12/2005 | |
| WO | WO-2005123034 A2 * | 12/2005 | ........... A61K 9/1623 |
| WO | 2006113594 A1 | 10/2006 | |
| WO | 2011011873 A1 | 2/2011 | |

OTHER PUBLICATIONS

Msd Animal Health Gmbh: "Paracox 8 ad us. Vet." Sep. 30, 2010 (Sep. 30, 2010), XP055282820 (Year: 2010).*
European Search Report for patent application 15203012.8, dated Jul. 6, 2016, 8 pages.
International search report for PCT/EP2016/082530, dated Feb. 15, 2017, 13 pages.
Irish Medicines Board: "Summary of Product Characteristics Paracox", https://www.hpra.ie/img/uploaded/swedocuments/LicenseSPC_10996-245-001_29082011165942.pdf, XP055282943, retrieved from internet Jun. 22, 2016.
MSD Animal Health GmbH: Paracox 8 ad us. vet., www.vetpharm.uzh.ch/tak/00000000/00001397.VAK, XP055282820, retrieved from Internet Jun. 22, 2016.
Williams, R.B., The origins and biological significance of the coccidial lesions that occur in chickens vaccinated with a live attenuated anticoccidial vaccine, Avian Pathology, 2001, 215-220, 30.
Shimokita brand research and development center test research report No. 3, 2004, pp. 48-50, https://www.aomori-itc.or.jp/_files/00037129/3_48-50.pdf (references showing wellknowntechnology).
Heping, Li (Editor), Principles and Technologies of Fine Chemical Production, Henan Science and Technology Press, 1994, 315-316, Section 3.
Heping, Li (Editor), Principles and Technologies of Fine Chemical Production, Henan Science and Technology Press, 1994, 315-316, Section 3—English Translation.

* cited by examiner

*Primary Examiner* — Jana A Hines
(74) *Attorney, Agent, or Firm* — Michael D. Davis

(57) ABSTRACT

The present invention relates to an improved vaccine against Coccidiosis in poultry. The vaccine comprises live *Eimeria* oocysts in a composition with relatively high viscosity because of the inclusion of between 0.3 and 1.5% w/v Xanthan gum. Upon spray vaccination the new vaccine forms beads that are quickly ingested by the birds and which provide a rapid vaccine take, resulting in a quick and effective improvement of the signs of Coccidiosis upon challenge infection.

Also the invention relates to a method for the heat sterilisation of a composition comprising Xanthan gum; by the inclusion of a concentration of a metal salt, an irreversible and dramatic reduction in viscosity can be largely prevented.

4 Claims, No Drawings

COCCIDIOSIS VACCINE

CROSS-REFERENCE TO RELATED APPLICATIONS

This application is a divisional application of co-pending U.S. application Ser. No. 16/064,027, filed on Jun. 20, 2018, which is a national stage entry under 35 U.S.C. § 371 of PCT/EP2016/082530 filed on Dec. 23, 2016, which claims priority to EP 15203012.8 filed on Dec. 29, 2015, the contents of which are hereby incorporated by reference in their entireties.

The present invention relates to the fields of veterinary parasitology and -vaccinology; more specifically the invention relates to a Coccidiosis vaccine for poultry comprising live *Eimeria* oocysts; to methods for the preparation of the Coccidiosis vaccine; to a kit of parts; and to methods of administration of the Coccidiosis vaccine.

*Eimeria* are protozoan parasites of the phylum Apicomplexa, and the class Coccidia, and occur worldwide. When infecting poultry, they cause a medium to severe enteric disease-complex, called: Coccidiosis. *Eimeria* have a complex lifecycle with multiple stages, some developing outside the host. *Eimeria* infection occurs by ingestion of sporulated oocysts and can happen from the first day of age. In the gut sporozoites are released which then colonize a section of the bird's intestine, by invading gut epithelial cells. Replication leads to release of merozoite stages, and rupture of gut-epithelial cells from the host. Next the merozoites re-infect further epithelial cells, and this continues for up to another four cycles of 4-6 days. Finally the sexual stages develop, which produce oocysts that are released with the faeces. After sporulation in the environment the cycle starts anew (Shirley et al., 2005, Adv. in Paras., vol. 60, p. 285).

The major species of *Eimeria* that infect poultry can be identified in a number of ways, routinely by microscopic size and appearance of the coccidia. Also, the different *Eimeria* species tend to colonise different areas of the avian intestines.

Symptoms of *Eimeria* infection in poultry vary from loss of appetite to bloody diarrhoea and organ failure due to build-up of necrotic tissue in the intestines. Consequences are a drop in feed conversion rate, reduced growth rate, reduced egg production, and susceptibility to secondary infections, all causing major discomfort to affected birds, and serious economic damage to a commercial poultry operation.

Protection against *Eimeria* infection and Coccidiosis can be based on administering anti-coccidial drugs (coccidiostats) via the feed, but build-up of resistance and presence of drug-residues in animal products are a constant concern. Therefore *Eimeria* infection and subsequent disease in poultry is preferably combated by vaccination. Next to subunit- and recombinant DNA vaccines, most employed are live vaccines, comprising sporulated oocysts from one or more species of *Eimeria*. Their natural replication in the bird induces a strong immunity, by both humoral and cellular routes of the immune system. Commonly a single vaccination early in life—helped by occasional wild type booster infections—is sufficient to protect the birds for their lifetime.

The live coccidia can be of wild type or of attenuated pathotype. A special class of attenuated *Eimeria* are the so-called precocious strains, which are *Eimeria* that will complete their lifecycle in a bird in fewer than normal number of cycles. These produce lower numbers of oocyst output and also less damage to a target's intestine. For an overview of poultry Coccidiosis, see: "The Merck veterinary manual" (10th ed., 2010, C. M. Kahn edt., ISBN: 091191093X), or: Swayne et al., eds.: "Diseases of Poultry", 13th ed., Wiley-Blackwell, Ames, Iowa, USA.

The efficacy of an *Eimeria* vaccine is usually determined by comparing the main criteria for infection and disease: gut lesion score, reduction of oocyst output, and effect on weight gain, after a challenge infection with a virulent *Eimeria* strain. A paper describing the relevance of these criteria for assessing *Eimeria* vaccine efficacy is: Williams & Catchpole, (2000, Vaccine, vol. 18, p. 1178-1185).

Typically a live *Eimeria* vaccine will contain sporulated coccidia from several *Eimeria* species, as immunity is species specific. For example some commercial Coccidiosis vaccines for poultry are: from MSD Animal Health, the vaccine lines: Coccivac™, Paracox™, or Fortegra™, which contain live sporulated coccidia from different strains of up to 8 species of *Eimeria*. Other commercial *Eimeria* vaccines are Immucox™ (Ceva), and Inovocox™ (Zoetis).

Such vaccines are commonly administered by some method of mass vaccination in order to reduce costs, such as by spray to the body or the feed, or via the drinking water. Because field infection pressure exists from the first day of age, therefore vaccination is preferably applied as young as possible. This can conveniently be done by spray administration at the hatchery, when chicks have just hatched and are kept in open trays. This route reaches the body of the birds as well as their direct surroundings. The vaccine is then ingested by the birds via oral-, nasal, or ocular route by their tendency to peck-up droplets and to preen their feathers.

The main concern in live coccidial *Eimeria* vaccination is to optimise the vaccine take, i.e. the quick and comprehensive ingestion by the birds, to allow the coccidia to quickly establish an infection in the bird's intestines and thus induce a protective immune-response. Thus there is an urgent need in the field to further improve the ingestion and effectiveness of coccidial *Eimeria* vaccines.

Several improvements have already been made. For example, to stimulate ingestion, spray vaccines are commonly provided with a bright colour such as green (chlorophyll) or red (carmine). The bright colour enhances visibility and appeals to the birds' curiosity, which stimulates pecking and preening.

One problem of *Eimeria* spray vaccines is that coccidia are relatively large and heavy micro-organisms (15-30 μm diameter oval shapes), and therefore have a tendency to settle in liquid carriers under influence of gravity. This is especially disadvantageous when the vaccine applied uses *Eimeria* of different species, which may have different sized coccidia; the heavier species then tend to settle more quickly and may not be ingested to the full amount required. To overcome this, existing vaccines may contain a rheology modifier as a suspending aid. For example the Paracox™ 8 vaccine contains 0.3% w/v Xanthan gum per animal dose. This keeps the different coccidia suspended and mixed evenly during administration. However, the viscosity of this vaccine is low.

Xanthan gum is a high molecular weight polysaccharide that is produced by bacteria of the *Xanthomonas* genus. These days it is produced by the industrial fermentation of *X. campestris* on for instance whey. Xanthan gum is used in a variety of products, such as pharmaceuticals and foods, as a stabiliser of emulsions, or as a thickener to influence a product's viscosity. Xanthan gum is a pseudoplastic, i.e. it has shear-thinning properties. It is available from different commercial suppliers, e.g. as Keltrol™ from CP Kelco. Details and properties of Xanthan gum are described for example in the 'Xanthan book', $8^{th}$ ed., 2008, cpkelco.com.

To improve the ingestion of coccidial *Eimeria* vaccines, other adaptations have been applied, such as formulating the vaccine composition as a highly viscous gel. For example WO 2005/099.617 describes a coccidial *Eimeria* vaccine that is provided as a soft gel containing about 1% carrageenan, which is a seaweed-derived polysaccharide, commonly used in the food industry for its gelling properties. However for administration of this gel onto chickens, a special delivery system is required, a 'gel dispenser' with a special manifold that produces a stream of gel-droplets.

A further development of this carrageenan soft gel formulation for the spray administration of viral- or bacterial vaccines is described in WO 2011/011.873: by adding about 0.1% w/v Xanthan gum per dose, the soft gel droplets were more sticky. However the special delivery apparatus is still required.

It is therefore an object of the present invention to overcome a disadvantage in the prior art, and to accommodate to a need in the field by providing a live coccidial *Eimeria* spray vaccine that provides improved vaccine efficacy, and can be delivered by conventional spray apparatus.

Surprisingly it was found that this object can be met, and consequently one or more disadvantages of the prior art can be overcome and improved upon, by providing a live *Eimeria* coccidia based Coccidiosis vaccine comprising 0.3-1.5% w/v Xanthan gum, which provides the vaccine with a relatively high viscosity. The new vaccine demonstrated significantly improved efficacy, as compared to a similar vaccine that did not have this concentration of Xanthan gum.

The advantageous results are that the new Coccidiosis vaccine is quickly and comprehensively ingested by the birds, resulting in an improved vaccine take (level of replication of vaccine coccidia in the gut). This, because the time from ingestion to initiation of the first round of replication was significantly reduced. Further the new vaccine can be delivered with a conventional spray apparatus such as a standard hatchery spray cabinet or a back-pack sprayer. Also, the vaccine composition does not need constant stirring during the spray administration. In addition, the droplets formed from the new vaccine do not wet the chicks upon spray vaccination, preventing the negative side-effects of chilling, especially for day-old chicks.

Although the inventor does not want to be bound by any theory or model that might explain these findings, he speculates that this vaccine composition has a viscosity that—upon application as a spray—allows the formation of beads of a size that is attractive to the birds for pecking up, whereby the vaccine's ingestion is more rapid and comprehensive than for the less viscous *Eimeria* spray vaccines of the prior art. In addition the coccidia displayed a reduced time for gut-transit and establishment of an infection, possibly as an effect of the encapsulation by the Xanthan gum polysaccharide, which helps the ingested coccidia to more readily establish themselves in the birds intestines, and so lead to an earlier development of immunity.

A Coccidiosis vaccine of this composition has a relatively high viscosity of between about 200 and about 4000 mPa·s, which upon administration as a coarse spray, was found to be ideally suited to produce beads of a size between about 1 and about 4 mm in diameter. Beads of this size (especially when highly visible from a colorant) appeared to be very appealing to the birds and were quickly and effectively ingested.

Higher or lower Xanthan gum concentrations did not provide correct bead formation upon spray: at concentrations of Xanthan gum higher than about 1.5% w/v, no separated beads were produced, and at concentrations of Xanthan gum lower than about 0.3% w/v, the spray was too wet, not giving good beads and causing wetting and chilling of the birds.

In spite of the relatively high viscosity, the new vaccine does not require the use of specialised spraying equipment. This is probably the result of the pseudoplastic properties of Xanthan gum.

Therefore in one aspect the invention relates to a Coccidiosis vaccine for poultry, comprising live oocysts of at least one species of *Eimeria* in a pharmaceutically acceptable carrier, characterised in that the vaccine comprises 0.3-1.5% w/v Xanthan gum which gives the vaccine a viscosity between 200 and 4000 mPa·s.

"Coccidiosis" is well known as an intestinal disease-complex caused by coccidial parasites, such as *Eimeria*.

A "vaccine" is well known to be a composition that has an inherent medical effect. A vaccine comprises an immunologically active component, and a pharmaceutically acceptable carrier. The 'immunologically active component', is one or more antigenic molecule(s), here: live *Eimeria* coccidia, that are recognised by the immune system of a target, and induces a protective immunological response. The response may originate from the targets' innate- and/or from the acquired immune system, and may be of the cellular- and/or of the humoral type.

A vaccine generally is efficacious in reducing the level or the extent of an infection, for example by reducing the parasitic load or shortening the duration of the parasite's replication in a host animal.

Also, or possibly as a results thereof, a vaccine generally is effective in reducing or ameliorating the (clinical) symptoms of disease that may be caused by such infection or replication, or by the animal's response to that infection or replication.

The effect of a Coccidiosis vaccine according to the invention is the prevention or reduction in poultry of an infection by an *Eimeria* and/or of one or more signs of Coccidial disease that are associated with such infection or replication. Here such (clinical) signs are: intestinal lesions, bodyweight gain, and oocyst output.

Such a Coccidiosis vaccine may colloquially also be referred to as a vaccine 'against' *Eimeria* or against Coccidiosis, or as an '*Eimeria* vaccine'.

Details and preferences of a Coccidiosis vaccine according to the invention will be described herein below.

"Poultry" refers to avians of agricultural relevance, such as: chicken, turkey, duck, goose, partridge, peacock, quail, pigeon, pheasant, guinea fowl, or ostrich.

The term "comprising" (as well as variations such as "comprise", "comprises", and "comprised") as used herein, intends to refer to all elements, and in any possible combination conceivable for the invention, that are covered by or included in the text section, paragraph, claim, etc., in which this term is used, even if such elements or combinations are not explicitly recited; and not to the exclusion of any of such element(s) or combinations.

Therefore any such text section, paragraph, claim, etc., can therefore also relate to one or more embodiment(s) wherein the term "comprising" (or its variants) is replaced by terms such as "consist of", "consisting of", or "consist essentially of".

"oocysts" are well known micro-organisms that are one of the life-cycle stages of an Apicomplexan parasite such as an *Eimeria*.

The oocysts are "live" when they are capable of initiating an *Eimeria* replicative cycle under the appropriate conditions, such as in the intestines of a bird.

An "*Eimeria*" is well known in the art as a parasite belonging to the Eimeriidae family. These parasites and their induced diseases are described in well-known handbooks (supra). An *Eimeria* displays the characterising features of its taxonomic group-members such as the morphologic, genomic, and biochemical characteristics, as well as the biological characteristics such as physiologic, immunologic, or pathologic behaviour.

As is known in the field, the classification of a micro-organism as a particular "species" is based on a combination of such features. The invention therefore also includes *Eimeria* that are sub-classified therefrom in any way, for instance as a subspecies, strain, isolate, genotype, variant, subtype or subgroup and the like.

The *Eimeria* for the invention can replicate in a species of poultry, and for example comprise, but are not limited to, the *Eimeria* species: *E. acervulina, E. tenella, E. maxima, E. brunetti, E. mitis, E. mivati, E. necatrix, E. praecox, E. hagani, E. meleagrimitis* (type 1 and type 2), *E. adenoides, E. gallopavonis, E. dispersa, E. innocua, E. subrotunda*, and *E. meleagridis*.

It will be apparent to a skilled person that while a particular *Eimeria* for the invention may currently be assigned to a specific species and genus, that is a taxonomic classification that could change in time as new insights can lead to reclassification into a new or different taxonomic group. However, as this does not change the micro-organism itself, or its antigenic repertoire, but only its scientific name or classification, such re-classified micro-organisms remain within the scope of the invention.

*Eimeria* parasites for use in the invention can be obtained from a variety of sources, e.g. as original field isolates from a poultry house, or as reference- or laboratory strain from various laboratories and (depository) institutions.

The "at least one species" refers to the practice to include *Eimeria* of more than one species in a coccidial *Eimeria* vaccine, to provide broad immune protection. In addition the vaccine can comprise one or more strains of a particular species, to cover differences in prevalence.

A "pharmaceutically acceptable carrier" for the invention is a liquid of a high grade of purity and sterile, for example water, a physiological salt solution, or a phosphate buffered saline solution. In a more complex form the carrier can e.g. be a buffer comprising further additives, such as stabilisers or preservatives. However for the present invention there is a limit to the concentration of salt that can be comprised in the final vaccine. This is for reasons of maintaining a palatable composition. Details are described in relation to the method for preparation and the sterilisation of Xanthan gum described below.

A "Xanthan gum" is the well-known polysaccharide that is generally available commercially, in several qualities and purities, for example as Keltro™, Xantura™, or Kelzan™, from CP Kelco.

For the invention the concentration of the Xanthan gum is determined as "% w/v", i.e. a percentage in weight-per-volume. This is to be determined on the basis of the final vaccine composition as it is in an animal dose ready for administration to the birds.

This does not exclude that the vaccine according to the invention or parts thereof may be produced, marketed, or stored in a more concentrated form, e.g. concentrated 2 or more times, which is then diluted to the final use concentration shortly before administration. This may be advantageous for stability, or for logistic reasons, to reduce volume and save costs for packaging and transportation.

By the incorporation of a concentration of Xanthan gum between 0.3 and 1.5% w/v, the resulting vaccine composition acquires a relatively high viscosity of between 200 and 4000 mPa·s, respectively.

Viscosity can be measured using a variety of suitable equipment; for the invention, preferred method of viscosity measurement is by using the rotating spindle technique, whereby the samples are measured when equilibrated at a constant temperature, e.g. 25° C. Details are described in the Examples section.

Preferably, the vaccine composition does not contain any other rheology modifier such as a polysaccharide, gum, gelling agent, or thickener that can substantially raise the viscosity of an aqueous vaccine composition, besides Xanthan gum. Evidently, this is aside from any minor effects on viscosity that may be caused by other vaccine ingredients such as salt, buffer, antigenic protein, adjuvant, etc.

Therefore, in an embodiment of the Coccidiosis vaccine according to the invention, the Xanthan gum is the only rheology modifier in the vaccine composition.

In an embodiment the Coccidiosis vaccine according to the invention comprises 0.4-1.2% w/v Xanthan gum. Preferably the vaccine comprises 0.5-1% w/v Xanthan gum, 0.5-0.9% w/v, 0.5-0.8% w/v, or even 0.5-0.7% w/v Xanthan gum, in that order of preference.

In an embodiment, the Coccidiosis vaccine according to the invention comprises about 0.6% w/v Xanthan gum.

For the invention, "about" indicates that a number can vary between ±25% around its indicated value. Preferably "about" means ±20% around its value, more preferably "about" means ±15, 12, 10, 8, 6, 5, 4, 3, 2% around its value, or even "about" means ±1% around its value, in that order of preference.

In an embodiment the target poultry for the Coccidiosis vaccine according to the invention is selected from the group consisting of chicken, turkey, duck, and geese. In a preferred embodiment the poultry is chicken or turkey, because for these poultry species the economic impact on the poultry sector of *Eimeria* infection is the largest. Most preferred is chicken.

The target birds may be of any type such as layers, breeders, broilers, combination breeds, or parental lines of any of such breeds. Preferred type is broilers.

The vaccine according to the invention can in principle comprise any *Eimeria* coccidia that is capable of infecting or replicating in a poultry.

In an embodiment of the Coccidiosis vaccine according to the invention, the live *Eimeria* coccidia are from an attenuated strain of *Eimeria.*

Attenuated *Eimeria* can be obtained by selection of naturally occurring *Eimeria* differing in pathogenicity. Alternatively attenuated *Eimeria* can be obtained by in vitro passaging and selection, or via recombinant DNA technology, all well known in the art.

In a preferred embodiment, the attenuated *Eimeria* are precocious.

Preferably the Coccidiosis vaccine according to the invention comprises the same coccidia species as present in an existing commercial live coccidia based *Eimeria* vaccine; more preferred: the same coccidia as in the group consisting of the vaccine lines: Coccivac, Paracox, and Fortegra.

Therefore in an embodiment of a Coccidiosis vaccine according to the invention for chickens, the at least one species of *Eimeria* is one or more or all, selected from the group consisting of: *E. acervulina, E. tenella, E. maxima, E. brunetti, E. mitis, E. praecox, E. mivati, E. hagani*, and *E. necatrix*.

Similarly, in an embodiment of a Coccidiosis vaccine according to the invention for turkeys, the at least one species of *Eimeria* is one or more or all, selected from the group consisting of: *E. adenoeides, E. meleagrimitis* type 1, *E. meleagrimitis* type 2, *E. gallopavonis*, and *E. dispersa*.

The exact amount of *Eimeria* coccidia per dose of the vaccine according to the invention, is not so critical, because the coccidia will readily replicate and colonise the hosts intestine. The vaccine dose only needs to be sufficient to initiate such a productive infection. A higher inoculum dose hardly shortens the time it takes to reach the optimal colonisation in the host; and very high doses are not attractive for economic reasons. In addition, too high doses of vaccine coccidia may cause some pathology by themselves. Evidently, too low a dose, although perhaps capable of establishing an *Eimeria* infection, may take too much time for a proper onset of immunity.

A preferred inoculum dose is therefore between about $1 \times 10^1$ and about $1 \times 10^5$ sporulated oocysts of a species of *Eimeria* per animal dose, more preferably between $1 \times 10^2$ and $1 \times 10^4$ oocysts per dose, between 100 and 5000, or even between 100 and 1000 oocysts/animal dose, in that order of preference.

As will be apparent to the skilled person, the optimal vaccine dose will depend e.g. on the target animal species, and on the species and the virulence of the *Eimeria* strain used, and may therefore be different for the various *Eimeria* species in one combination vaccine.

Methods to count and quantify *Eimeria* coccidia for use in the Coccidiosis vaccine according to the invention are well known in the art.

The volume per animal dose of the Coccidiosis vaccine according to the invention can be optimised according to the intended route of application, e.g. for a body spray vaccination the dose may be between about 10 µl and 1 ml per bird. Preferably the volume of spray vaccine per bird is between 0.1 and 0.5 ml per bird, more preferably between 0.2 and 0.3 ml per bird.

Alternatively the vaccine can be administered by spray onto the feed, or as a liquid to the drinking water.

Finding the optimal volume and dose for the various routes of administration, by determining what is an immunologically effective amount of *Eimeria* coccidia per animal dose of vaccine according to the invention, is well within the routine capabilities of the skilled artisan.

Determining the effectiveness of a Coccidiosis vaccine according to the invention can e.g. be done by monitoring the immunological response following vaccination or after a challenge infection, e.g. by monitoring the targets' signs of disease, clinical scores, serological parameters, or by re-isolation of the pathogen, and comparing these results to a vaccination-challenge response seen in mock vaccinated animals.

The age, weight, sex, immunological status, and other parameters of the target poultry for the Coccidiosis vaccine according to the invention, are not critical although it is evidently favourable to vaccinate healthy targets, and to vaccinate as early as possible to prevent (the consequences of) an early infection by a pathogenic *Eimeria*.

Therefore, the Coccidiosis vaccine according to the invention is preferably administered at the day of hatch (i.e. at 1 day old).

Occasionally the poultry may be given a booster vaccination later in life.

It is highly efficient to formulate the vaccine according to the invention as a combination vaccine, because in this way multiple immunologic agents can be administered at once, providing a reduction of discomfort to the vaccinated target birds, as well as of the time and labour costs. A combination vaccine comprises in addition to the Coccidiosis vaccine according to the invention, another immunologically active compound. In principle this can be any live or killed micro-organism or subunit product, provided this does not reduce the stability or the replicative capacity of the *Eimeria* coccidia. Also, the additional immunoactive component(s) must be compatible with the intended oral route of applicating the Coccidiosis vaccine. The additional immunologically active compound may be an antigen, an immune enhancing substance, a cytokine, and/or a vaccine Alternatively, the Coccidiosis vaccine according to the invention, may itself be added to a vaccine.

Depending on the characteristics of the particular form of the Coccidiosis vaccine according to the invention, the way to make a further combination needs to be carefully selected. Such choices are within the routine capabilities of the skilled person.

Therefore, in an embodiment, the vaccine according to the invention is characterised in that the vaccine comprises one or more additional immunoactive component(s).

In an embodiment the vaccine according to the invention is a combination vaccine, comprising at least one additional antigen derived from a micro-organism that is pathogenic to poultry. The additional antigen may be a live, live attenuated, or killed micro-organism, or a part—or subunit antigen thereof.

Preferably the additional antigen from a micro-organism that is pathogenic to poultry is one or more, selected from the groups consisting of:

Viruses: infectious bronchitis virus (IBV), Newcastle disease virus (NDV), adenovirus, egg drop syndrome virus, infectious bursal disease virus (IBDV) (i.e. Gumborovirus), chicken anaemia virus, avian encephalomyelitis virus, fowl pox virus, turkey rhinotracheitis virus (TRT), duck plague virus (duck viral enteritis), pigeon pox virus, Marek's disease virus (MDV), avian leucosis virus, infectious laryngo-tracheitis virus ILTV), avian pneumovirus, avian influenza virus (AIV), and reovirus;

Bacteria: *Escherichia coli, Salmonella, Ornitobacterium rhinotracheale, Haemophilis paragallinarum, Pasteurella multocida, Erysipelothrix rhusiopathiae, Erysipelas, Mycoplasma, Campylobacter, Shigella*, and *Clostridium;*

Parasites: *Histomonas, Isospora, Cryptosporidium*, and *Dermanyssus*; and

Fungi: *Aspergillus*.

Most preferred additional antigen is selected from: IBV, NDV, IBDV, ILTV, TRT, AIV, MDV, *Mycoplasma*, and *Salmonella*.

In an embodiment of a Coccidiosis vaccine according to the invention, the additional immunoactive component is an adjuvant.

An "adjuvant" is a well-known vaccine ingredient, which in general is a substance that stimulates the immune response of a target bird in a non-specific manner. Many different adjuvants are known in the art.

Evidently the adjuvant should be mild enough not to affect the stability or replicative potential of the live *Eimeria* coccidia.

In a preferred embodiment the adjuvant is a cytokine.

A Coccidiosis vaccine according to the invention can advantageously be combined with a pharmaceutical component such as an antibiotic, a hormone, and/or an anti-inflammatory drug.

The use of an anti-coccidial compound is also possible, provided that the *Eimeria* coccidia in the vaccine are not sensitive to that particular drug.

The Coccidiosis vaccine according to the invention may contain one or more components that aid the viability and quality of the live *Eimeria* coccidia for use in the invention, thereby promoting the productive replication and establishment of a colonisation in the intestines of target poultry.

The additive may be a stabiliser, to stabilise the quantity and the quality of an *Eimeria* coccidia for the invention during storage, handling, administration or ingestion. Generally stabilisers are large molecules of high molecular weight, such as lipids, carbohydrates, or proteins; for instance milk-powder, gelatine, serum albumin, sorbitol, trehalose, spermidine, dextrane or polyvinyl pyrrolidone.

Also suitable preservatives may be added, such as thimerosal, merthiolate, phenolic compounds, or gentamicin.

A Coccidiosis vaccine according to the invention can be used either as a prophylactic- or as a therapeutic treatment, or both, as it interferes both with the establishment and with the progression of an infection by an *Eimeria*.

As is described below in great detail: as a result of certain choices in the manufacturing process of the Coccidiosis vaccine according to the invention, the vaccine composition may contain a certain concentration of a metal salt. In short: this can be required to stabilise the Xanthan gum when it needs to be sterilised by heating. However for maintaining the palatability of the beads of the Coccidiosis vaccine according to the invention, the salt concentration should not exceed a level of 0.4% w/v in the final vaccine composition.

Therefore in an embodiment of the Coccidiosis vaccine according to the invention, the vaccine comprises less than about 0.4% w/v metal salt.

In an embodiment of the Coccidiosis vaccine according to the invention, one or more or all of the conditions apply selected from the group consisting of:
  the vaccine comprises an adjuvant, preferably an immuno-stimulatory oligodeoxynucleotide;
  the vaccine comprises an additional antigen from a microorganism that is pathogenic to poultry, preferably one or more selected from: IBV, NDV, IBDV, ILTV, TRT, AIV, MDV, *Mycoplasma*, and *Salmonella;*
  the at least one species of *Eimeria* is one or more or all, selected from the group consisting of: *E. acervulina, E. tenella, E. maxima, E. brunetti, E. mitis, E. praecox, E. hagani,* and *E. necatrix;*
  the *Eimeria* is attenuated;
  the *Eimeria* is precocious;
  the vaccine is for chicken;
  the poultry is one day old;
  the vaccine comprises less than about 0.4% w/v metal salt; and
  the vaccine comprises about 0.6% w/v Xanthan gum.

The Coccidiosis vaccine according to the invention can be prepared from live *Eimeria* coccidia by methods well known and readily applicable by a person skilled in the art. For example: *Eimeria* parasites are produced industrially in donor poultry animals, and isolated from their faeces by well-known techniques such as centrifugation and salt flotation, followed by sporulation and sterilisation, and finally counting by light microscopy. Sporulation can be performed e.g. using potassium-dichromate, and sterilisation can be done using sodium-hypochlorite or beta-propiolactone. The sporulated *Eimeria* oocysts are then formulated with a pharmaceutical carrier into a vaccine and the final product is apportioned into appropriate sized containers and packaged.

The various stages of the manufacturing process are monitored by adequate tests, for instance by immunological tests for the quality and quantity of the coccidia or other antigens; by microbiological tests for inactivation (if applicable), sterility and absence of extraneous agents; and ultimately by in vitro or in vivo experiments to determine vaccine efficacy and -safety. All these are well known to a skilled person, and are prescribed in Governmental regulations such as the Pharmacopoeia, and in handbooks such as: "Remington: the science and practice of pharmacy" (2000, Lippincot, USA, ISBN: 683306472), and: "Veterinary vaccinology" (P. Pastoret et al. ed., 1997, Elsevier, Amsterdam, ISBN 0444819681).

Therefore in a further aspect the invention relates to a method for the preparation of a Coccidiosis vaccine according to the invention, characterised in that the method comprises the step of admixing live oocysts of at least one species of *Eimeria* in a pharmaceutically acceptable carrier, with Xanthan gum up to 0.3-1.5% w/v.

The Xanthan gum may be admixed with the coccidia as a powder. Preferably however, the Xanthan gum is admixed as a solution. That allows for a composition with Xanthan gum to be prepared separately from a composition comprising the *Eimeria* coccidia. Similarly, a composition comprising the coccidia may be prepared and stored separately in a concentrated form, to be mixed with the Xanthan gum shortly before use. This provides flexibility in production planning and logistics, and can assist in maintaining the stability of the coccidia.

Effectively the composition comprising Xanthan gum then serves as a diluent for a concentrated composition of coccidia. However, and as will be clear to the skilled person, upon the admixing of two compositions, such as one with the coccidia and one with the Xanthan gum, a dilution occurs of both these compositions. Consequently, to arrive at a specific final concentration of coccidia and Xanthan gum in the resulting Coccidiosis vaccine according to the invention, the compositions being mixed need to be of higher than final strength to allow for this dilution.

For example, when the two types of compositions are mixed at equal volumes, both need to be at double the desired final concentration of their components; e.g. the composition comprising the Xanthan gum in this case would need to comprise between 0.6 and 3.0% w/v Xanthan gum.

Therefore in an embodiment the method for the preparation of a Coccidiosis vaccine according to the invention, is characterised in that the Xanthan gum is provided in a composition of which the concentration is such that after the admixing the resulting vaccine comprises 0.3-1.5% w/v Xanthan gum.

In an advantageous application, this allows the vaccine according to the invention to be supplied as a kit of parts for preparing the Coccidiosis vaccine according to the invention, wherein the kit comprises separate containers, one with live coccidia, and one with Xanthan gum that is to be used as a diluent for the coccidia, and whereby the containers combined can be used to prepare the vaccine according to the invention.

Therefore in a further aspect the invention relates to a kit of parts for preparing a Coccidiosis vaccine according to the invention, characterised in that the kit comprises at least two containers: one container comprising a composition comprising live oocysts of at least one species of *Eimeria* in a pharmaceutically acceptable carrier, and one container comprising a composition comprising Xanthan gum, whereby the concentration of the composition comprising Xanthan gum is such that after combining the compositions of both containers, the resulting vaccine comprises 0.3-1.5% w/v Xanthan gum.

In a preferred embodiment, the kit of parts according to the invention comprises instructions for the use of said kit and/or the preparation of the Coccidiosis vaccine according to the invention.

The instructions for use, comprised with the kit of parts according to the invention, may for example be provided by way of information written on, or attached to, one or all of the container(s), or on a box containing one or all of the container(s). Also the instructions may be present on a leaflet packaged with one or all of the container(s), such as a patient information leaflet or a package insert. Also, the instructions for use may be provided by way of a reference to instructions in electronic form, such as information viewable on, or downloadable from, an internet website from the distributor of the kit, and the like.

The kit of parts according to the invention, may also be an offer of the mentioned parts (relating to commercial sale), for example on an internet website, for combined use in a method for preparation of the Coccidiosis vaccine according to the invention.

In the practice of the preparation of a commercial form of the Coccidiosis vaccine according to the invention, there was a further problem to be solved. This was because for obtaining marketing authorisation, commercial vaccines commonly have to be prepared sterile.

Several possibilities for large scale sterilisation of vaccine components (evidently excluding any live vaccine microorganism) exist, and these are commonly verified by spiking samples of the vaccine with different indicator micro-organisms, and detecting their complete inactivation after the sterilisation method.

Common methods are micro-filtration or gamma irradiation. For the present invention, the separation of the vaccine components in a kit of parts allows for the separate sterilisation of the composition comprising Xanthan gum.

However, filtration and irradiation are relatively expensive methods, which is a serious disadvantage for a poultry vaccine. Therefore another common method for the sterilisation of vaccine components is preferred: heat sterilisation (autoclaving). This is efficient and cheap at large scale. However, when preparing the Coccidiosis vaccine according to the invention, the inventor was initially disappointed to find that the Xanthan gum was inactivated when heat sterilised as such: as is described in the Examples section, when subjected to a heat sterilisation protocol that is standard in vaccine manufacturing, a solution of 0.6% w/v Xanthan gum in water displayed a dramatic and irreversible loss of its viscosity: from above 600 mPa·s to 25 mPa·s. A Coccidiosis vaccine prepared with this autoclaved Xanthan gum solution with low viscosity, could no longer produce the required beads of vaccine upon spray administration.

With this discovery, it can now be understood why the commercial vaccine Paracox 8 only has a low viscosity, in spite of it containing 0.3% w/v Xanthan gum per animal dose: the components of this vaccine (other than the coccidia) are heat sterilised before their final combination. This causes the unintended, and previously unnoticed, inactivation of the Xanthan gum. In retrospect this also explains why applying Paracox 8 vaccine as a body spray does not produce beads of vaccine favourable for effective ingestion, and causes wetting of the birds.

The inventor then found a way to allow the heat sterilisation of a composition comprising Xanthan gum without destroying its viscosity. Surprisingly it was found that this object can be met, and consequently one or more disadvantages of the prior art can be overcome, by providing a composition comprising Xanthan gum with a concentration of a metal salt of at least about 0.1% w/v; the % w/v in this case is to be calculated over the volume of the composition comprising the Xanthan gum and the metal salt.

The metal salt was found to be able to effectively protect a composition comprising Xanthan gum during heat sterilisation against a severe (more than 15%) and irreversible loss of viscosity.

Therefore in a further aspect, the invention relates to a method for the heat sterilisation of a composition comprising Xanthan gum, characterised in that the method comprises admixing said composition with at least 0.1% w/v metal salt.

For the invention, a "heat sterilisation" involves an incubation for at least 15 minutes at at least 100° C. The metal salt in principle can be any metal salt, but preferably the metal salt is a salt from a mono- or bi-valent metal cation. More preferred the cation is an alkali-metal.

The anion of the metal salt is preferably a halogen, sulphate, phosphate, nitrate, or acetate. More preferred a chloride.

Even more preferred, the metal salt is a halogen salt of an alkali-metal; even more preferably of sodium or potassium; even more preferably the metal salt is: a sodium-chloride, or a potassium-chloride.

For the stabilisation of Xanthan gum during heat sterilisation by metal salt, there is no distinct upper limit to the concentration of metal salt, except that concentrations above about 5% w/v can be impractical to work with because of crystal formation, and corrosive properties.

In addition it was found that when applied to the preparation of a Coccidiosis vaccine according to the invention, beads produced upon spray administration which had a relatively high salt concentration were no longer readily ingested by the birds; probably because of a lack of palatability. An acceptance limit for the metal salt content of the vaccine beads was found to be at about 0.4% w/v of the final vaccine composition.

Therefore in an embodiment the method for the preparation of a Coccidiosis vaccine according to the invention, is characterised in that the composition comprising Xanthan gum additionally contains a concentration of a metal salt of at least about 0.1% w/v.

Preferably the concentration of the metal salt in the composition comprising Xanthan gum is such that the resulting vaccine comprises less than about 0.4% w/v metal salt.

In an embodiment of the method for the preparation of a Coccidiosis vaccine according to the invention, one or more or all of the conditions apply selected from the group consisting of:
  the metal salt is a sodium-chloride, or a potassium-chloride;
  in the composition comprising Xanthan gum and metal salt, the concentration of metal salt is such that after the admixing, the resulting vaccine comprises less than about 0.4% w/v metal salt;
  the vaccine comprises an adjuvant, preferably an immuno-stimulatory oligodeoxynucleotide;
  the vaccine comprises an additional antigen from a microorganism that is pathogenic to poultry, preferably one or more selected from: IBV, NDV, IBDV, ILTV, TRT, AIV, MDV, *Mycoplasma*, and *Salmonella*;

the at least one species of *Eimeria* is one or more or all, selected from the group consisting of: *E. acervulina, E. tenella, E. maxima, E. brunetti, E. mitis, E. praecox, E. hagani*, and *E. necatrix*;

the *Eimeria* is attenuated;

the *Eimeria* is precocious;

the vaccine is for chicken;

the poultry is one day old; and the resulting vaccine comprises about 0.6% w/v Xanthan gum.

Similarly the components of the kit of parts according to the invention can be adapted to this embodiment. Therefore in an embodiment the kit of parts according to the invention is characterised in that the composition comprising Xanthan gum additionally contains a concentration of a metal salt of at least about 0.1% w/v, and the concentration of the metal salt in said composition is such that the resulting vaccine comprises less than about 0.4% w/v metal salt.

In an embodiment of the kit of parts according to the invention, one or more or all of the conditions apply selected from the group consisting of:

the metal salt is a sodium-chloride, or a potassium-chloride;

in the composition comprising Xanthan gum and metal salt, the concentration of metal salt is such that after the combination of the components of the kit, the resulting vaccine comprises less than about 0.4% w/v metal salt;

the vaccine comprises an adjuvant, preferably an immuno-stimulatory oligodeoxynucleotide;

the vaccine comprises an additional antigen from a microorganism that is pathogenic to poultry, preferably one or more selected from: IBV, NDV, IBDV, ILTV, TRT, AIV, MDV, *Mycoplasma*, and *Salmonella*;

the at least one species of *Eimeria* is one or more or all, selected from the group consisting of: *E. acervulina, E. tenella, E. maxima, E. brunetti, E. mitis, E. praecox, E. hagani*, and *E. necatrix*;

the *Eimeria* is attenuated;

the *Eimeria* is precocious;

the vaccine is for chicken;

the poultry is one day old; and the resulting vaccine comprises about 0.6% w/v Xanthan gum.

Depending on the circumstances of the administration of the vaccine according to the invention, e.g. the route and the target poultry species, it may be necessary to further adapt the vaccine composition. This is well within the capabilities of a skilled person, and generally involves the fine-tuning of the efficacy or the safety of the vaccine. This can be done by adapting the vaccine dose, quantity, frequency, or the route, by using the vaccine in another form or formulation, or by adapting the other constituents of the vaccine (e.g. stabilisers, carriers, adjuvants, diluents, and the like). Typically when applied as coarse spray, a coccidial *Eimeria* vaccine may be mixed with a colouring agent.

For reasons of stability or economy a Coccidiosis vaccine according to the invention may be prepared in freeze-dried form. In general that will enable prolonged storage at temperatures above zero ° C., e.g. at 4° C. Procedures for freeze-drying are known to persons skilled in the art, and equipment for freeze-drying at different scales is available commercially. Evidently, the *Eimeria* parasite should be in a relatively robust form to survive the freezing, drying, storage, and thawing periods. Therefore a favourable embodiment is to freeze-dry the sporozoite form of the *Eimeria* for use in the invention.

Therefore, in an embodiment of a method for the preparation of a vaccine according to the invention, the vaccine is prepared in a freeze-dried form.

The Coccidiosis vaccine according to the invention, and methods for its preparation according to the invention, with all their advantageous implications, can also be described in alternate wording, focussing on the surprising and advantageous medical uses of the vaccine composition:

Therefore in a further aspect the invention relates to a composition comprising live oocysts of at least one species of *Eimeria* in a pharmaceutically acceptable carrier for use as a Coccidiosis vaccine for poultry, characterised in that the composition comprises 0.3-1.5% w/v Xanthan gum which gives said composition a viscosity between 200 and 4000 mPa·s.

Also:

In a further aspect the invention relates to the use of a composition comprising live oocysts of at least one species of *Eimeria* in a pharmaceutically acceptable carrier for the manufacture of a Coccidiosis vaccine for poultry, characterised in that the composition comprises 0.3-1.5% w/v Xanthan gum which gives said composition a viscosity between 200 and 4000 mPa·s.

The Coccidiosis vaccine according to the invention is preferably administered to the target birds in an optimal way in respect of its dose, volume, route, and formulation, as well in an optimal way with respect to the target's age, sex, or health status. The skilled person is perfectly capable of determining such optimal conditions for the vaccine administration.

In an embodiment, the Coccidiosis vaccine according to the invention is applied via a method of mass application, such as by spray, on the body or the feed, or via the drinking water. This reduces both the discomfort of vaccination to the target birds, as well as the labour costs.

Suitable methods for the mass administration of Coccidiosis vaccine according to the invention, should of course be compatible with a live *Eimeria* coccidium, and aim for reaching the intestines. Preferred methods are: by spray, or drinking water, or by (automated) injection into the egg, so-called in ovo vaccination. Suitable equipment for mass administration of a poultry vaccine is available commercially.

Therefore in a further aspect the invention relates to a method of vaccination of poultry against Coccidiosis, characterised in that the method comprises administering the Coccidiosis vaccine according to the invention to said poultry as a body spray.

The indication of the vaccine being a "body spray" does not require that all of the body of the birds is covered, it merely indicates that no particular part of the body needs to be specifically targeted. In addition, a significant part of the vaccine delivered in this way will not land on, or stay on, the body of the birds, but may end up on the floor. This is fine, as the birds will quickly start to peck at such droplets and ingest them.

The advantageous properties of the Coccidiosis vaccine according to the invention, when delivered to the body of the birds, are most prominent when applied as a coarse spray. In that case vaccine beads form that are quickly ingested by the birds from the feathers or the floor.

Therefore in an embodiment, a method of vaccination of poultry according to the invention is characterised in that the spraying is applied as a coarse spray.

Generally a coarse spray applies droplet of a size over 50 µm in diameter. For the present invention, the droplets are preferably between 1 and 4 mm in size. By selecting the equipment used, such as the nozzle and the pressure used, a skilled person can conveniently arrive at droplets of such sizes.

Such a coarse spray can for example be applied using a hatchery sprayer when immunising day old chicks in hatching trays, or can be applied e.g. using a back-pack type sprayer when immunising older birds in a floor pen setting.

The administration regime for applying the vaccine according to the invention to a target bird can be in single or in multiple doses, in a manner compatible with the formulation of the vaccine and with practical aspects of the animal husbandry.

Preferably, the regimen for a method of vaccination of poultry according to the invention is integrated into existing vaccination schedules of other vaccines that the target birds may require, in order to reduce stress to the animals and to reduce labour costs. These other vaccines can be administered in a simultaneous, concurrent, or sequential fashion, in a manner compatible with their registered use.

Therefore in an embodiment of a method of vaccination of poultry according to the invention, the vaccine is administered in a combination with another poultry vaccine.

The advantageous medical effects as described herein, of the Coccidiosis vaccine according to the invention can also be covered using different wording:

In a further aspect the invention relates to a method for the prevention or reduction of an infection with *Eimeria* or of associated signs of disease in poultry, characterised in that the method comprises the administration to said poultry of a Coccidiosis vaccine according to the invention.

The invention will now be further described by the following, non-limiting, examples.

EXAMPLES

Example 1: Comparison of Viscosity of Xanthan Gum Compositions

The viscosity of a solution of Xanthan gum in water was determined under different conditions, testing the effect of heat sterilisation with or without the inclusion of a concentration of metal salt.

Some of the samples were autoclaved, by incubation for 30 minutes at 115° C.

Viscosity measurements were performed with a Brookfield™ rotational viscometer according to the manufacturer's instructions. This equipment determines the viscosity of a liquid from the torque on a spindle, rotating at a defined number of rotations per minute, in a defined volume of that liquid. All samples were measured while equilibrated in a water bath at 25° C.

TABLE 1

Viscosity of a solution of Xanthan gum in water

| % w/v Xanthan gum | Pre-treatment | Additive | Viscosity (mPa · s) |
| --- | --- | --- | --- |
| 0.6 | autoclaved | none | 25.5 |
| 0.6 | autoclaved | 0.15% w/v NaCl | 593 |
| 0.6 | autoclaved | 0.15% w/v NaCl and 0.1% Carmine | 586 |

TABLE 1-continued

Viscosity of a solution of Xanthan gum in water

| % w/v Xanthan gum | Pre-treatment | Additive | Viscosity (mPa · s) |
| --- | --- | --- | --- |
| 0.6 | none | 0.15% w/v NaCl and 0.2% Carmine | 660 |
| 2.4 | autoclaved | 0.15% w/v NaCl | 8061 |

These results demonstrate that the addition of a specific concentration of metal salt can almost completely prevent the otherwise dramatic decrease in viscosity that occurs upon heat sterilisation of a Xanthan gum dilution in water. The difference in viscosity between the samples autoclaved+salt and not-autoclaved+salt (here: about 11%), is considered to be non-severe.

Example 2: Effect of Xanthan Gum on Efficacy of a Multi-Species Live Coccidial *Eimeria* Vaccine 2.1. Introduction:

To improve the delivery of a day-old coarse body spray administration of live Coccidiosis vaccines, the inventor tested a Xanthan gum vaccine formulation, next to a more traditional vaccine wherein the coccidia were diluted in water. It was tested if the vaccine would 'bead' on the birds, increasing the visibility of the vaccine, and leading to better vaccine ingestion and minimal wetting of the birds.

2.2. Experimental Design

One hundred and twenty, one day-old chickens were divided into three groups of 40. All birds in group 1 were vaccinated with coccidia corresponding to those of the Paracox™ 8 vaccine, in water; the birds in group 2 were vaccinated with the same type of coccidia but in 0.6% w/v Xanthan Gum/0.2% w/v Nacl, and with 0.1% w/v Carmine (E120); both by coarse spray. Birds in group 3 were not vaccinated (see Table 2). All birds were kept in groups in separate floor pens for 21 days post vaccination. For the monitoring of (vaccinal) oocyst shedding, faecal samples were collected from the floor pens: for the vaccinated birds (groups 1 and 2) daily from day 4 to day 14 and on day 20 post vaccination (pv); for the control birds (group 3) on days 7, 14 and 20.

On day 21 pv, thirty birds per group were uniquely identified by numbered tag, then each bird was challenged with 15,000 oocysts of a virulent *E. tenella* wild type strain. Next the challenged birds were transferred to collection cages (3 cages of 10 birds per group) in containment rooms. The remaining birds in groups 1 & 2 were euthanized and discarded. The remaining birds in group 3 were left in the floor pen to be weighed on days 21, 28 and 35. Two birds were not vaccinated and not challenged, to allow detection of any non-experimental infection.

On day 5 post challenge (pc), in total 10 challenged birds (3 from each cage of the first two groups, and 4 from the third group) were euthanized and examined post mortem (without knowing the treatment group) for lesions associated with an *E. tenella* infection.

On day 7 pc all remaining birds were weighed and a bulked faecal collection was taken from all cages, for enumeration of oocyst output. On day 14 pc all birds were weighed before being euthanized.

Throughout the study all birds were observed daily for clinical signs related to an *Eimeria* infection, such as diarrhoea or bloody faeces, depression, or inappetance; no non-experimental infections were observed.

2.3. Materials and Methods

2.3.1. Test Animals

Chickens used were SPF, of mixed sex, and one day old at the start of the experiment. All birds were checked for being of apparent good health and size before vaccination. The birds were allocated to the groups in a randomised way, on a first caught basis. Tap water and standard feed were available ad libitum. Challenge inoculation was by oral gavage.

2.3.2. Test Materials

Vaccine coccidia (as in Paracox 8) and challenge materials (sterile, sporulated oocysts of E. tenella) were kept at 2-8° C. until use, and were well within their expiry date at the time of the experiment.

The Paracox 8 vaccine coccidia were diluted to provide one animal dose in 0.21 ml; the vaccine for groups 1 and 2 were made up to contain 3,000 doses. The diluents were held in separate sterile glass Duran bottles either 315 ml of sterile water for group 1, or for group 2: 315 ml of (heat sterilised) 1.2% w/v Xanthan Gum (Xantural 11K, CP Kelco) and 0.4% w/v NaCl, both containing 0.2% w/v Carmine. Two, 5000 dose sachets were shaken and massaged vigorously for 1 minute to ensure re-suspension of the oocysts. The contents of these sachets were pooled. From the pooled vaccine 315 ml was taken and added to each of the diluents. Both formulations were then thoroughly mixed using a flea and magnetic stirrer for group 1, or shaken by hand for group 2, for at least 10 minutes prior to use.

The concentration of the oocysts in the challenge material was determined using a modified Fuchs-Rosenthal counting chamber. From this a dilution was made to provide 15.000 oocysts per animal dose of 0.5 ml.

2.3.3. Spray Vaccination

A Spraycox™ II machine was used following the manufacturer's instructions, to apply a coarse spray vaccine to the chicken hatchlings. As the machine is designed to vaccinate 100 chicks per tray, for the 40 chicks per groups used here, the tray area was reduced by 60%. A paper tray liner was used to provide a good surface which allowed the birds to move freely and preen themselves and each other.

The target was to administer 0.21 ml of vaccine per bird, therefore 21 ml of vaccine was applied per tray. Prior to vaccination, the Spraycox machine's settings were calibrated by several mock runs to ensure that the correct dose (21 ml) was dispensed over the total internal surface area of the tray before the vaccination of the groups in the experiment. The prepared vaccines were shaken for 10 minutes prior to being transferred to the Spraycox machine, to ensure thorough mixing of the vaccine. Once vaccinated, birds were kept for at least 30 minutes in the trays in which they were vaccinated, in a well-lit and warm area before being transferred to the floor pens. The birds were monitored during this time to see how quickly the vaccine was taken up. Between each vaccination, the spray machine's settings were re-confirmed, and the machine was thoroughly rinsed out with warm water. The groups were vaccinated in order i.e. group 1 before 2.

2.3.4. Faecal Samples

Post challenge, bulked faecal samples were collected from challenged cages between days 4 and 7 post challenge. The sample from each cage was separately collected on plastic sheets to determine the total oocyst output after challenge. Faeces were sprayed with water at least daily to ensure that they were kept moist. Each sample was double bagged, labelled to identify the contents, and stored at 2-8° C. until processing. The oocysts were recovered as per standard practices and the numbers calculated using the McMaster counting technique.

2.3.5. Data Analysis

Data on the lesion scores, bodyweight gain, and oocyst output from pens of vaccinated challenged birds (groups 1 and 2) were compared with each other and with the control group (unvaccinated-challenged-group 3), using statistical tests. All analyses were performed by a statistician using SAS™ 9.3 with a significance level of 5%.

2.4. Results

2.4.1. Lesion Scores

Lesions associated with E. tenella were determined by post mortem examination at day 5 pc. Results are summarised per group (n=10) in Table 2. Scoring was performed as described in the European Pharmacopoeia monograph 2326. In short: a score of 0 means no gross lesions, and scores of 1-4 mean increasing severity of thickening of the intestinal wall, increased amounts of blood, and decreased amounts of normal faeces. At a lesion score of 4 there can even be some mortality.

The results show that the lesion scores in groups 1 and 3 were significantly higher than those in group 2 (P<0.0001), only overlapping at a score of 2. Although the birds in groups 1 and 3 only had high scores (2 or greater) the scores for the birds in group 1 were generally lower than the scores of the birds in group 3, however these are not significantly different to each other (P=0.6917).

TABLE 2

Effect of vaccinations and challenge on lesion scores

| Group - feature | Lesion score (number of birds) | | | | |
|---|---|---|---|---|---|
| | 0 | 1 | 2 | 3 | 4 |
| 1 - vaccine in water | — | — | 1 | 6 | 3 |
| 2 - vaccine in Xanthan gum | 3 | 5 | 2 | — | — |
| 3 - unvaccinated | — | — | 2 | 3 | 5 |

2.4.2. Bodyweight Gain

Individual bodyweights were recorded on day 21 prior to challenge, and on days 7 and 14 pc, before euthanasia. A summary of weight measurement results per group (n=20) is presented in Table 3.

The data shows that the birds in both of the vaccinated groups (1&2) gained significantly more weight than those in group 3, at 7 days pc (P<0.001—both groups) and at 14 days pc (P<0.001—both groups). With group 2 also gaining significantly more weight than group 1 at both time points (challenge+7 days: P=0.017; challenge+14 days: P=0.034).

TABLE 3

Effect of vaccinations and challenge on bodyweight

| Group - feature | Average bodyweight (g) | | | Average bodyweight gain (g) | |
|---|---|---|---|---|---|
| | d. 21 pv | d. 7 pc | d. 14 pc | d. 0-7 pc | d. 0-14 pc |
| 1 - vaccine in water | 191.23 | 274.43 | 375.45 | 83.20 | 184.22 |
| 2 - vaccine in Xanthan gum | 203.37 | 300.80 | 406.75 | 97.43 | 203.38 |
| 3 - unvaccinated | 176.74 | 208.49 | 312.35 | 31.75 | 135.62 |

2.4.3. Oocyst Output

The amounts of oocysts detected in the faecal collections are summarised in Tables 4 (taken post vaccination) and 5 (post challenge). Post vaccination there is good oocyst output showing that the vaccination was successful. Also the patterns of the oocyst output are as expected: an initial peak in oocyst output, directly resulting from the vaccination, followed by a drop in output, followed by a second peak, six days after the first, as the oocysts go through their second cycle. In group 2 the initial peak in oocyst output, although smaller than that in group 1, is earlier by three days and results in a larger second peak.

Because immunity to coccidial *Eimeria* vaccines is strongly linked to oocyst cycling, therefore the birds in group 2 (vaccine in Xanthan gum) had a stronger immunity at the time of challenge infection, compared to group 1 (vaccine in water). The improved initial ingestion of the vaccine, and the reduced gut-transit time for the Xanthan gum containing vaccine, thus leads to a better and earlier development of immunity against Coccidiosis.

TABLE 4

Effect of vaccination on oocyst output post vaccination.

| Group - feature | Number of oocysts/gram faeces (×10^3) at X days pv |  |  |  |  |  |  |  |  |  |  |
|---|---|---|---|---|---|---|---|---|---|---|---|
|  | 4 | 5 | 6 | 7 | 8 | 9 | 10 | 11 | 12 | 13 | 14 | 20 |
| 1 - vaccine in water | 0 | 0 | 0 | 2 | 5 | 0 | 1 | 0.5 | 1 | 1.5 | 12 | 5.5 |
| 2 - vaccine in Xanthan gum | 0 | 3 | 0 | 0 | 0 | 4 | 5 | 33 | 8 | 15 | 1 | 3 |
| 3 - unvaccinated | 0 | 0 | 0 | 0 | 0 | 0 | 0 | 0 | 0 | 0 | 0 | 0 |

Post challenge, there are clear numerical differences in the oocyst output between the groups, these differences are statistically significant with group 2 shedding significantly less oocysts than the other two groups ($P < 0.0001$). There is no statistically significant difference between the shedding by groups 1 and 3 ($P = 0.0651$).

TABLE 5

Effect of vaccination and challenge on oocyst output post challenge.

| Group - feature | Number of oocysts/gram faeces (×10^6) |
|---|---|
| 1 - vaccine in water | 23.0 |
| 2 - vaccine in Xanthan gum | 0.43 |
| 3 - unvaccinated | 35.9 |

2.5. Conclusions

The data support the conclusion that the use of Xanthan gum significantly improves the efficacy of an existing multi-species live coccidial *Eimeria* vaccine. The vaccine delivered in the Xanthan gum formulation provided greater immunity to the birds against challenge at 21 days post vaccination, as compared to the same vaccine but delivered in water. All of the three parameters used to assess vaccination efficacy: lesion scores, increase in bodyweight gain, and reduction of oocyst output, were significantly improved for the group receiving the vaccine in Xanthan gum, as compared to the traditional vaccine in water group and to the unvaccinated control group.

While the vaccine had been prepared using heat-sterilised Xanthan gum, this had been provided with a concentration of metal salt so as to stabilise it during the heating.

The strongly improved vaccine efficacy is due to an improved ingestion of vaccine, delivered in the Xanthan gum, demonstrated by the earlier output of vaccinal oocysts and improved re-cycling. This lead to an impressive reduction in lesion scores and oocyst output, as well as to an economically highly relevant increase in bodyweight gain post challenge.

Example 3: Improved Vaccine Take

In an experiment of smaller scale, but otherwise highly similar in design and performance to the experiment described in Example 2, the efficacy of the vaccine take of a Coccidiosis vaccine according to the invention was compared to a standard vaccine without Xanthan gum.

For such an experiment, 'vaccine take' is determined at 5-7 days post vaccination, at post mortem, by a microscopic examination of scrapings from the intestinal-wall. To detect the various species of *Eimeria*, different regions of the gut need to be monitored.

When comparing a Coccidiosis vaccine according to the invention using 0.6% w/v Xanthan gum, and a vaccine based on Paracox 8 (i.e. coccidia in water), an improvement of the vaccine take was observed: from about 40-60% take for the coccidia in water, up to almost 80% take for the coccidia in Xanthan gum.

Example 4: Effect of Different Spray Formulations

In early experiments, different gel-formulations for the delivery of coarse spray administration of live coccidiosis vaccines to day-old chicks were tested. The experiments compared solutions comprising either 3% polyvinylpyrrolidone (PVP) of type K-90, or 0.6% Xanthan gum in water. The negative control had the coccidia in plain water. All three formulations contained Carmine colorant (E120) at a final concentration of 0.1% w/v. The formulations were not heat-sterilised, consequently no salt was added.

4.1. Experimental Set-Up

The experimental set-up was highly similar in design and performance to the experiment described in Example 2. In short: 75, day-old SPF chickens were randomly allocated to three groups of 25 birds. Each group was vaccinated with *E. tenella* by coarse spray, administered at a dose level of 0.21 ml, i.e about 500 coccidia per bird, using a commercial Spraycox II machine. The vaccine coccidia used were of the *E. tenella* strain as is present in the Paracox product.

Post vaccination the birds were left to preen and take up the vaccine; they were then transferred to isolators at 1 group per isolator, and brooded for 7 days. Birds were observed daily. At 7 days p.v. the birds were euthanased and examined post mortem for the presence of oocysts or developing stages in their gut.

Vaccine uptake was determined by microscopical examination of wet smears from both caecal pouches. Scores were either positive or negative depending on the presence or absence of parasitic stages, see Table 6.

4.2. Results

The results obtained showed a clear advantage for the formulation with Xanthan gum over the two other formulations tested.

TABLE 6

| | Effect of gel-formulation on vaccine uptake: | | |
|---|---|---|---|
| Group | Positive birds | Negative birds | % Vaccine uptake |
| 1: Water | 12 | 10 | 54.5 |
| 2: 0.6% Xanthan gum | 17 | 7 | 70.8 |
| 3: 3% PVP K-90 | 10 | 13 | 43.5 |

4.3. Conclusions

The uptake of the vaccine, as confirmed through the presence of parasitic stages seen in wet Cecal smears, is affected by the formulation in which it is applied. The use of 0.6% Xanthan gum (group 2) improved the uptake of the vaccine by 30%, namely from 54.5% with the traditional water medium (group 1) to 70.8%. Conversely the use of 3% PVP (group 3) actually reduced the uptake of vaccine by 20%, when compared with the water group, namely from 54.5 to 43.5%.

Consequently, the use of the 0.6% Xanthan gum in the formulation of a spray vaccine of Eimeria oocysts has a clear positive effect on the uptake of oocysts, compared to the use of 3% PVP, or the use of conventional plain water as medium.

Because all formulations tested contained Carmine, this experiment also demonstrated that the positive effect of Xanthan gum is distinctly separate from that of the colorant.

Similarly, because no salt was added, this proves that presence of salt is not required when there is no heat-sterilisation.

The invention claimed is:

1. A method of vaccinating poultry against Coccidiosis, wherein the method comprises administering to poultry a Coccidiosis vaccine via a body spray;
    wherein the Coccidiosis vaccine comprises live oocysts of at least one species of *Eimeria* in a pharmaceutically acceptable carrier;
    wherein the vaccine comprises 0.3-1.5% w/v Xanthan gum that has been heat-sterilized in the presence of a concentration of a metal salt of at least about 0.1% w/v;
    wherein the Coccidiosis vaccine comprises less than about 0.4% w/v metal salt; and
    wherein the Coccidiosis vaccine has a viscosity of between 200 and 4000 mPa·s.

2. The method of vaccinating poultry against Coccidiosis of claim 1, wherein the body spray is applied as a coarse spray.

3. The method of vaccinating poultry against Coccidiosis of claim 1, wherein the at least one species of *Eimeria* is selected from the group consisting of: *E. acervulina, E. tenella, E. maxima, E. brunetti, E. mitis, E. praecox, E. mivati, E. hagani, E. necatrix*, and any combination thereof.

4. The method of vaccinating poultry against Coccidiosis of claim 3, wherein the body spray is applied as a coarse spray.

* * * * *